(12) United States Patent
Lam et al.

(10) Patent No.: US 7,015,023 B1
(45) Date of Patent: Mar. 21, 2006

(54) COMPOSITIONS AND METHODS FOR DETECTION OF ACTIVE PROTEASES

(75) Inventors: Eric Lam, East Brunswick, NJ (US); Olga del Pozo, Seville (ES)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 10/009,472

(22) PCT Filed: May 2, 2000

(86) PCT No.: PCT/US00/11893

§ 371 (c)(1), (2), (4) Date: Mar. 29, 2002

(87) PCT Pub. No.: WO00/66615

PCT Pub. Date: Nov. 9, 2000

Related U.S. Application Data

(60) Provisional application No. 60/132,358, filed on May 4, 1999.

(51) Int. Cl.
*C12P 21/06* (2006.01)
*C12N 9/00* (2006.01)
*C12N 9/42* (2006.01)
*C07H 21/04* (2006.01)

(52) U.S. Cl. .............. 435/209; 435/4; 435/6; 435/69.1; 435/69.7; 435/183; 435/200; 435/252.1; 435/320.1; 435/336; 435/334; 435/219; 536/23.2; 536/23.4; 530/350

(58) Field of Classification Search ............... 530/350; 435/183–230, 4, 8–20, 7.4, 69.1, 69.7, 336, 435/334; 536/23.2
See application file for complete search history.

(56) References Cited

U.S. PATENT DOCUMENTS 5,599,906 A * 2/1997 Dasmahapatra
5,861,161 A    1/1999 Cohen et al. ............ 424/192.1

OTHER PUBLICATIONS

Hawkins et al. PNAS, vol. 96:2885-2890, Mar. 1999.*
Xu et al. Nucleic Acids Res., Apr. 15, 1998, vol. 26(8):2034-2035.*
Mattioni et al. (Methods in Cell Biol., vol. 43:335-352, 1994).*
Hull et al. (Methods in Mol. Biol., 1995, vol. 49:125-141).*
Evans et al., "Expression and characterization of chimeric rDNA proteins engineered for purification and enzymatic cleavage", *Protein Expr. Purif.* 1991 2:205-213.
Fields et al., "The two-hybrid system:an assay for protein-protein interactions", *Trends Genet.* 1994 10(8):286-292.
Liebig et al., "Proteinase trapping:Screening for viral proteinase mutants by α complementation", *Proc. Natl. Acad. Sci. USA* 1991 88:5979-5983.

* cited by examiner

*Primary Examiner*—Manjunath N. Rao
(74) *Attorney, Agent, or Firm*—Licata & Tyrrell P.C.

(57) ABSTRACT

A novel assay system is disclosed for detecting the presence or amount of selected active proteases in biological samples. The assay system utilizes a chimeric protease detector protein composed of three domains: (1) a repressor domain, (2) a protease cleavage domain specific for the protease to be assayed, and a reporter domain. The reporter domain is not detectable when linked to the repressor domain, but becomes detectable upon release from the repressor domain by protease-mediated cleavage. Thus, the activity of the selected protein can be determined by measuring the amount of detectable reporter in the sample. Methods and test kits for using the novel assay system in a variety of in vitro and in vivo applications are also disclosed.

7 Claims, 6 Drawing Sheets

—□— RET
—◇— RET + CASP1
······○······ RET + CASP1 + Ac-YVAD-CMK
—△— TGUS-YVAD-HBD C
--⊞-- TGUS-YVAD-HBD + CASP1
···◆·· TGUS-YVAD-HBD + CASP1 + Ac-YVAD-CMK
······○······ TGUS-YVAA-HBD C
--▽-- TGUS-YVAA-HBD + CASP1
···□·· TGUS-YVAA-HBD + CASP1 + Ac-YVAD-CMK

# COMPOSITIONS AND METHODS FOR DETECTION OF ACTIVE PROTEASES

This application claims priority to U.S. Provisional Application No. 60/132,358, filed May 4, 1999, the entirety of which is incorporated by reference herein.

FIELD OF THE INVENTION

This invention relates to the field of detection and measurement of biological molecules. In particular, the invention provides a novel assay system for detecting the presence or amount of selected active proteases in biological samples.

BACKGROUND OF THE INVENTION

Various scientific articles are referred to in parentheses throughout the specification, and complete citations are listed at the end of the specification. These articles are incorporated by reference herein to describe the state of the art to which this invention pertains.

Proteases are ubiquitous enzymes that play important roles in the control of cellular processes. In eukaryotes, proteases play key roles in orchestrating the progression of the cell cycle as well as in the decision process for activating programmed cell death. For example, it has become clear in the past 10 years that a large number of distinct but related cysteine proteases, called caspases, are involved in cell death activation in animals (Cryns and Yuan, 1998). From gene knock-out studies in mice, it is quite clear that different caspases play distinct roles in the cell death control of various tissues. In addition, although aspartate is the invariant residue at the P1 position of their target sites, animal caspases can be distinguished from each other by their preference of distinct substrate peptide sequences (Talanian et al. 1997). The ability to monitor the presence of different caspases in vivo should greatly facilitate our understanding of how this family of important protease may be controlled at the level of their enzymatic activity.

Many other proteases also recognize distinct targets for cleavage of proteins. These include cathepsin G, papain and thrombin, to name a few.

One in vivo approach for monitoring protease activity is the technology of Fluorescence Resonance Energy Transfer (FRET). In the approach described by Heim and Tsien (1995), two fluorescent proteins, Green Fluorescent Protein (GFP) and Blue Fluorescent Protein (BFP) are linked by a 25 amino acid linker with a trypsin cleavage site. FRET from BFP to GFP can be demonstrated with the fusion protein and is lost upon trypsin addition. The lost of FRET is measured as a decrease of green fluorescence with the concomitant increase in blue fluorescence. Although this technique can in theory be used to detect the presence of proteases in vivo, the approach is likely to suffer from lack of sensitivity. Thus, if the activity of a particular protease in a cell is low or transient, the lost of FRET in a small percentage of the expressed GFP-BFP fusion proteins may be difficult to detect. Furthermore, the assay for FRET requires sophisticated and expensive equipment and background fluorescence of particular biological organisms (such as plants) may limit the application of this technology.

From the foregoing discussion, it can be seen that there is a need for economical and sensitive screening strategies for measuring the activities of selected proteases in vivo or in cell-free extracts. Such strategies would advance the field in several respects, which include facilitating the discovery of novel proteases and drugs that can modulate specific protease activities in different cellular contexts.

SUMMARY OF THE INVENTION

The present invention provides a novel assay system for measuring the activity of selected proteases in a variety of biological systems. The compositions and methods of the invention can be used in vivo or in cell-free assays to measure the activity of one or more selected proteases.

According to one aspect of the invention, a chimeric protein for detecting the presence or activity of a pre-determined protease is provided. The chimeric protein contains (a) a repressor domain which represses activity of a normally biologically active protein fused thereto; (b) a reporter domain comprising a protein having a detectable biological activity when not fused to the repressor domain; and (c) a protease cleavage domain linking the repressor domain to the reporter domain, the protease cleavage domain comprising a structure that is cleaved by activity of the pre-determined protease. In a preferred embodiment, the repressor domain is a hormone binding domain of a steroid hormone receptor, the reporter domain is β-glucuronidase and the protease cleavage domain is a cleavage site for a caspase.

In another embodiment, the chimeric protease detector protein comprises at least one repressor domain and a plurality of reporter domains, each linked to the repressor domain(s) by a protease cleavage site. Using a multiplicity of reporters and cleavage sites, this protease detector protein can be used to detect more than one selected protease.

According to another aspect of the invention, a method is provided for determining the presence or activity of a pre-determined protease in a biological sample, which utilizes the chimeric protease detector protein described herein. The method comprises adding the protease detector protein to the biological sample suspected of containing the pre-determined protease and measuring the detectable biological activity, if any, of the reporter domain. The occurrence and amount of the detectable biological activity is proportional to the occurrence and amount of the pre-determined protease in the biological sample.

The aforementioned method may be used in a biological sample comprises a biological fluid, tissue or cell extract by providing the protease detector protein as an isolated protein. Alternatively, the method can be used in a biological sample comprising intact cells in which the pre-determined protease, if present, is contained. In this instance, the protease detector protein is provided by introducing into the cells an expressible DNA construct that encodes the protein, under conditions whereby the protein is expressed. The DNA construct may be stably or transiently introduced into the cells.

According to another aspect of the invention, the above-described methods can be adapted for determining the presence or amount of a plurality of pre-determined proteases. This is accomplished by adding a plurality of protease detector proteins to the sample, each having a protease cleavage domain specifically cleaved by one of the pre-determined proteases, and each having a differentially detectable reporter domain. Alternatively, one or more modified protease detector proteins can be used, each comprising a repressor domain linked to two different protease cleavage domain, each protease cleavage domain being linked to a differentially detectable reporter domain.

In another aspect of the invention, the foregoing methods can be used in a screening assay to determine if a test compound affects the amount or activity of a pre-determined protease. In a typical screening assay, the selected protease and protease detector are combined in the presence or absence of the test compound, and the amount of detectable reporter is measured. An increase or decrease in detectable reporter production in the presence of the test compound is indicative of the ability of that compound to affect the amount or activity of the protease.

According to another aspect of the invention, test kits are provided for performing one or more of the assays described herein. The kits contain one or more of the protease detector proteins and, optionally, additional reagents and instructions for performing the assays.

Other features and advantages of the present invention will be better understood by reference to the drawings, detailed description and examples that follow.

BRIEF DESCRIPTION OF THE DRAWINGS

FIG. 2. Schematic diagram showing the method for the construction of the fusion proteins described in Example 1.

FIG. 4. Graphs showing GUS activity from in vitro translated samples using various constructs.

DETAILED DESCRIPTION OF THE INVENTION

Figure 1:
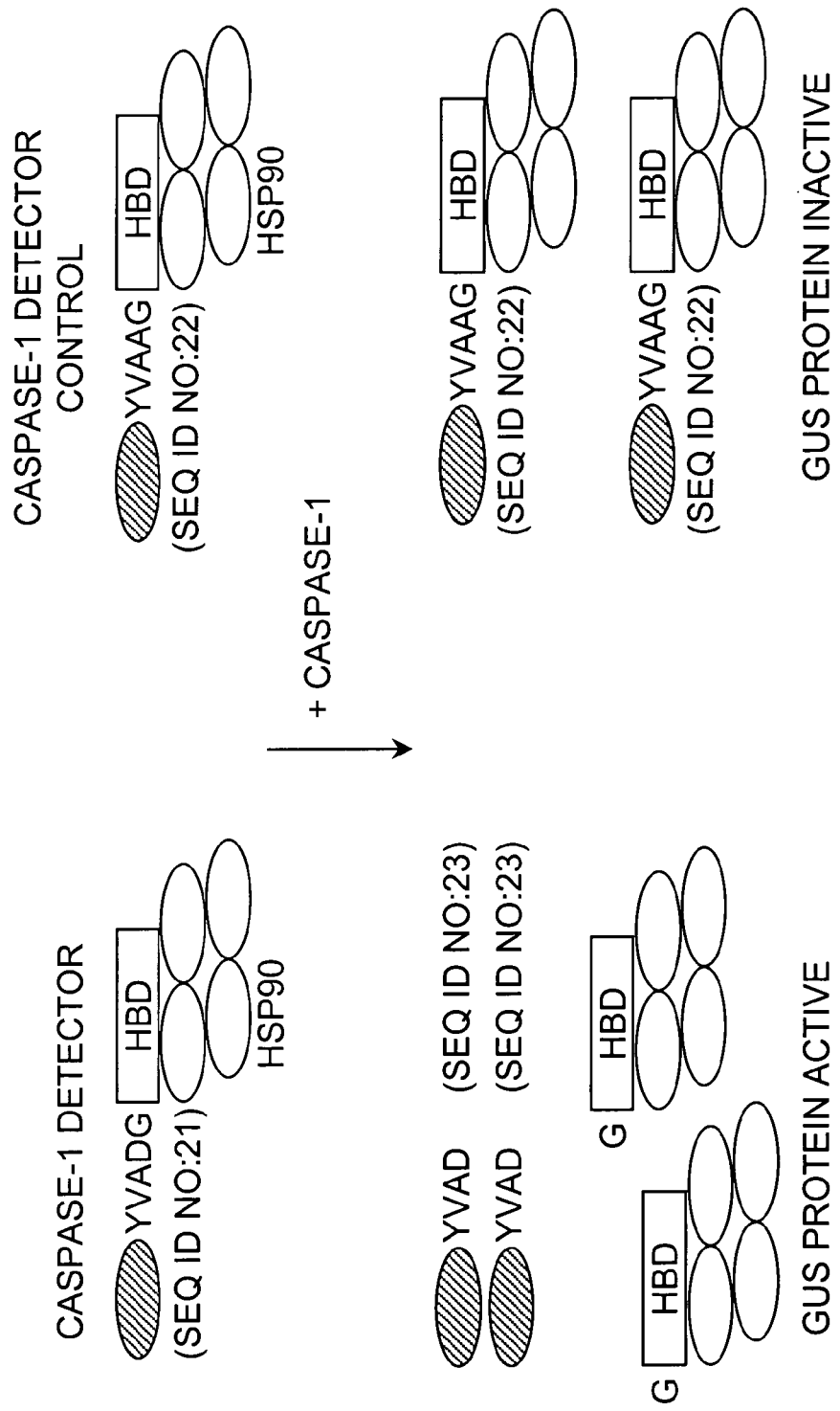
FIG. 1. Design of an exemplary protease detector of the present invention. The hormone binding domain (HBD) of the glucocorticoid receptor is fused to the β-glucuronidase (GUS) reporter gene. Between the proteins is introduced a protease recognition cleavage site. The GUS protein is inactive while attached to the HBD because it is unable to dimerize. The protease detector comprises a caspase-1 cleavage site. The control comprises a modified caspase-1 cleavage site, which is not recognized for cleavage by caspase-1. Upon addition of caspase-1 to the system, cleavage and release of GUS is observed in the protease detector, but not in the control.

I. Definitions:

Various terms relating to the present invention are used hereinabove and also throughout the specifications and claims.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A cell has been "transformed" or "transfected" by exogenous or heterologous DNA when such DNA has been introduced inside the cell. The transforming DNA (transgene) may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. If germline cells are stably transformed, the transformation may be passed from one generation of animals arising from the germline cells, to the next generation. In this instance, the transgene is referred to as being inheritable.

Other definitions are found in the description set forth below.

II. Description:

The present invention provides a sensitive and versatile detection system for proteases. The invention arises from the inventors' insight that the ligand binding domain of a certain class of cellular receptor molecules can be used to mask a well-characterized enzyme with activity that can normally be easily monitored. When a protease target site is positioned between these two domains of the chimera and the corresponding protease is added, the cleavage of the target sequence results in the appearance of the previously masked enzyme activity. The "gain-of-function" nature of this assay system provides high sensitivity and versatility in the monitoring of protease activities in vitro as well as in vivo.

The inventors have tested this novel strategy for the detection and monitoring of protease activities for in vitro and in vivo studies. As described in Example 1, the hormone binding domain (HBD) of the rat glucocorticoid receptor (GR) was fused to the bacterial enzyme β-glucuronidase (GUS) with a peptide sequence (Tyr-Val-Ala-Asp-Gly, SEQ ID NO:21) for caspase-1 cleavage inserted as a linker. When translated in vitro with rabbit reticulocyte lysates or expressed in transgenic plants (tobacco and *Arabidopsis*), the fusion of GUS to the HBD of GR resulted in complete inactivation of its enzymatic activity. In vitro, the inventors demonstrated that cleavage of GUS-GR by addition of caspase-1 leads to the release of the GUS protein from the GR domain with concomitant appearance of GUS activity. Introduction of a single point mutation in the P1 position of the caspase cleavage site (Tyr-Val-Ala-Ala-Gly, SEQ ID NO:22) abolished cleavage of the fusion protein by added caspase-1 and loss of GUS activation. These results illustrate the principle of the invention by demonstrating that HBD domains of steroid receptors can be used to inactivate enzyme activities of attached protein partners. The fusion junction in accessible to proteolytic enzymes, and cleavage by the appropriate protease leads to the separation of the HBD domain from the enzyme partner and results in the unmasking of the latent enzymatic activity.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (2000) (hereinafter "Ausubel et al.") are used.

The detection system of the invention utilizes a three-part chimeric protein, referred to herein as a "protease detector". The protease detector is composed of (1) a "repressor domain"; (2) a "reporter domain" comprising an enzyme that, when liberated from the repressor domain, has activity which is easily detectable; and (3) a protease cleavage domain that joins the repressor domain to the reporter domain. The protease detector is introduced into a test sample containing, or suspected of containing, a protease that specifically recognizes the protease cleavage domain. If present, the protease cleaves the chimeric detector at the cleavage domain, thereby liberating the reporter domain and allowing it to become active. Enzymatic activity of the reporter domain is detected, and the presence or amount of that activity is correlated to the presence or amount of the protease in the test sample.

The repressor domain can be any protein domain that represses the activity of a reporter enzyme to which it is linked via the protease cleavage domain. In preferred embodiments, repressor domains are taken from cellular receptors whose activity in cells is repressed until activated by binding of its cognate ligand. In accordance with the present invention, however, it has been found that, these repressor domains can act as ligand-independent repressors of activity of enzymes linked to them via a protease cleavage domain. Thus, the present invention differs in its fundamental nature from assays using ligand-activated receptors such as HBD, in that this system does not need to be activated by ligand binding to the receptor. Activation takes place only after protease cleavage.

The steroid hormone receptors are examples of cellular receptors whose binding domains provide particularly suitable repressor domains for use in the protease detector proteins of the invention. The steroid hormone receptors are members of a large family of important transcriptional regulators in animal systems. These proteins functions to transduce signals from steroid hormones to control cellular processes via the control of gene expression in the nucleus. The hormone binding domain (HBD) of the steroid receptor acts as a regulatory domain to control the function of the transcription factor domain (TFD). In the absence of the hormone, the HBD represses the activity of the TFD via the interaction with the heat shock protein HSF90. When hormone is present and binds to the HBD, the receptor is released from the HSP90 complex and the TFD is allowed to form a functional dimer and translocate into the nucleus to activate gene expression. It has been found that the HBD of steroid receptors such as the glucocorticoid receptor (GR) can function as an autonomous steroid regulatory domain hormone-binding domains (HBD) and can be used in various systems to confer steroid-dependent enzymatic activities (reviewed in Mattioni et al. 1994). In addition to animal cells, the HBD of GR has also been shown to confer dexamethasone-dependent transcription activities in higher plants (Simon et al. 1996; Aoyama and Chua 1997).

Another family of cellular receptors that contain suitable repressor domains is the bHLH/PAS superfamily of transcription regulators, exemplified by the aryl hydrocarbon receptor (AHR) and the hypoxia inducible factors (HIFα and HIF3α). The distinguishing characteristic of these proteins is a 200-300 stretch of amino acid sequence similarity known as a PAS (PER/ARNT/SIM) domain. The helix-loop-helix domain serves as a dimerization surface for AHR and ARNT and also positions the basic α-helix within the major groove of B-DNA to enable specific interactions with target enhancer elements. The PAS domain, a region of ~250 amino acids, functions as a dimerization surface, harbors a repressor region, and also contains regions required for binding agonist and forming interactions with Hsp90. The AHR resides primarily in the cytosol, where it is associated in an inactive form with a dimer of the molecular chaperone, Hsp90. Upon binding an agonist, the AHR dissociates from Hsp90, translocates to the nucleus and dimerizes with a structurally related protein, ARNT. This complex interacts with enhancer elements upstream of target promoters and up-regulates the transcription of a variety of xenobiotic metabolizing enzymes (e.g., the Cyt P450 encoded by CYP1A1). The AHR and ARNT are both members of the basic helix-loop-helix-PAS superfamily.

The reporter domain can be any domain that, when attached to the repressor domain through the protease cleavage domain, is substantially undetectable, but when detached from the repressor domain by protease cleavage, becomes detectable. Detectability can be by any means, but preferably relates to biological activity that is regained upon liberation of the reporter domain from the repressor domain. Examples of reporter domains suitable for use in the present invention include, but are not limited to, β-glucuronidase (GUS), β-galactosidase, chloramphenicol acetyl transferase (CAT), various transcription factors, alcohol dehydrogenase and luciferase.

The protease cleavage domain links the repressor domain to the reporter domain. This domain comprises a peptide sequence specifically recognized and cleaved by the protease whose activity is being assayed. A variety of proteases recognize specific cleavage sites in polypeptide sequences. Examples are set forth in the table below, which contains a list of characterized proteases and their specific substrates. Cleavage takes place between amino acid residue X and the P1 position for each of the target sites (X represents any amino acid) (Source: http//delphi.phys.univ-tours.fr/Prolysis/sublist.html and the catalog from Calbiochem Co.).

|  | Target site |  | SEQ ID |
|---|---|---|---|
| Protease | 3-letter code | 1-letter code | NO: |
| Calpain | Val—Leu—Lys—X | VLKX | 10 |
| Cathepsin G | Ala—Val—Pro—Phe—X | AVPFX | 11 |
| Collagenase | Pro—Gln—Gly—Ile—Ala—Gly—Gln—X | PQGIAGQX | 12 |
| Elastase I | Ala—Ala—Pro—Val—X | AAPVX | 13 |
| Elastase II | Ala—Ala—Pro—Ala—X | AAPAX | 14 |
| Granzyme B | Ala—Ala—Asp—X | AADX | 15 |
| MMP-1 | Pro—Gln—Gly—Ile—Ala Gly—Gln—Darg—X | PQGIAGQrX | 16 |
| Kallikrein | Pro—Phe—Arg—X | PFRX | 17 |
| Papain | Gln—Val—Val—Ala—Gly—Ala—X | QVVAGAX | 18 |
| Renin | Arg—Pro—Phe—His—Leu—Leu—Val—Tyr—X | RPFHLLVYX | 19 |
| Thrombin | Val—Pro—Arg—X | VPRX | 20 |
| Caspases | Preferred target site | SEQ ID NO: | |
| Caspase-1 | YVADX | 1 | |
| Caspase-2 | VDVADX | 2 | |
| Caspase-3 | DEVDX | 3 | |
| Caspase-4 | LEVDX | 4 | |
| Caspase-5 | WEHDX | 5 | |
| Caspase-6 | VEIDX | 6 | |
| Caspase-7 | VDQVDX | 7 | |
| Caspase-8 | IETDX | 8 | |
| Caspase-9 | LEHDX | 9 | |

It may be determined in some cases that, due to the size of the protease, the size of the cleavage site, or the selection of repressor or reporter domains, the protease cleavage domain is not efficiently cleaved by the protease. In this situation, the difficulty may be resolved by extending the protease cleavage site on one or both ends with an additional length of peptide, sometimes referred to herein as a "spacer" or a "linker".

The chimeric constructs of the invention are composed of proteins or peptides linked together. This may be accomplished in one of several ways known in the art, as summarized below.

Peptides may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. When solid-phase synthesis is utilized, the C-terminal amino acid is linked to an insoluble resin support that can produce a detachable bond by reacting with a carboxyl group in a C-terminal amino acid. One preferred insoluble resin support is p-hydroxymethylphenoxymethyl polystyrene (HMP) resin. Other useful resins include, but are not limited to: phenylacetamidomethyl (PAM) resins for synthesis of some N-methyl-containing peptides (this resin is used with the Boc method of solid phase synthesis; and MBHA (p-methylbenzhydrylamine) resins for producing peptides having C-terminal amide groups.

During the course of peptide synthesis, branched chain amino and carboxyl groups may be protected/deprotected as needed, using commonly-known protecting groups. In a preferred embodiment, $N^\alpha$-amino groups are protected with the base-labile 9-fluorenylmethyloxycarbonyl (Fmoc) group or t-butyloxycarbonyl (Boc groups). Side-chain functional groups consistent with Fmoc synthesis may be protected with the indicated protecting groups as follows: arginine (2,2,5,7,8-pentamethylchroman-6-sulfonyl); asparagine (O-t-butyl ester); cysteine glutamine and histidine (trityl); lysine (t-butyloxycarbonyl); serine and tyrosine (t-butyl). Modification utilizing alternative protecting groups for peptides and peptide derivatives will be apparent to those of skill in the art.

Full-length proteins or protein domains for use in the present invention may be prepared in a variety of ways, according to known methods. Proteins may be purified from appropriate sources, e.g., human or animal cultured cells or tissues, by various methods such as gel filtration, ion exchange chromatography, reverse-phase HPLC and immunoaffinity purification, among others. However, due to the often limited amount of a protein present in a sample at any given time, conventional purification techniques are not preferred in the present invention.

The availability of nucleic acids molecules encoding a protein enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. Example 1 describes the use of this methodology in constructing a protease detector comprising GUS, the HBD from GR and a caspase-1 cleavage site.

Alternatively, according to a preferred embodiment, a selected peptide or protein may be produced by expression in a suitable procaryotic or eucaryotic system. For example, a DNA molecule, encoding a peptide or protein component of the invention, or an entire chimeric protease detector molecule of the invention, may be inserted into a plasmid vector adapted for expression in a bacterial cell, such as *E. coli*, or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

A peptide or protein produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, so as to be readily purified from the surrounding medium. If expression/secretion vectors are not used, an alternative approach involves purifying the recombinant protein by affinity separation, such as by immunological interaction with antibodies that bind specifically to the recombinant protein. Such methods are commonly used for isolating peptides and proteins.

In an alternative embodiment, protein and/or peptide components of the invention are synthesized separately, then conjugated using standard methods known by those skilled in the art. For example, a synthetic peptide may be chemically coupled to a protein using m-maleimidobenzoyl-N-hydroxysuccinimide ester (MBF). This reagent cross-links amino- and carboxy-terminal thiol groups in the peptide with lysine side chains present in the protein. Alternatively, a synthetic peptide may be coupled to a protein using glutaraldehyde, a common cross-linking agent. Another method for chemically coupling a peptide to a protein is through the use of carbodiimide and 1-(3-dimethylaminopropyl)-3-ethylcarbodiimide methiodide (EDC). Methods for joining two proteins together are also available.

The peptides or proteins of the invention, prepared by the aforementioned methods, may be analyzed according to standard procedures. For example, they may be subjected to amino acid sequence analysis, mass spectra analysis or amino acid compositional analysis according to known methods.

The chimeric protease detector proteins of the present invention comprise two domains linked together by a protease cleavage site with or without linkers. The organization of the respective domains can differ. For instance, if "R" represents the repressor domain, "D" represent the detectable reporter domain, and "C" represents the protease cleavage domain (with or without linkers), the protease detector proteins of the present invention may be organized as follows:

D-C-R;
R-C-D;
$D_1$-$C_1$-R-$C_2$-$D_2$; wherein subscripted numbers indicated different cleavage sites or reporter domains. It should also be apparent that multiple repressor domains can be used in designing a complex protease detector protein.

The protease detector proteins of the present invention can be used singly or in combination to detect and quantitate activity of selected proteases in vitro and in vivo. The proteins can be used to assay various biological fluids, including tissue or cell extracts or environmental samples for activity of pre-determined proteases. Furthermore, in vitro detection of protease activation will enable the screening for drugs that affect cellular processes where proteases are activated either directly or upstream in a signal transduction pathway. The addition of appropriate substrates for the particular reporter enzyme in a microtiter plate will enable one to correlate protease activation with reporter enzyme activity. In the reverse approach, it can allow one to detect the presence of protease inhibitors or inhibitors of upstream components of the protease signaling pathway which normally leads to protease activation, thus rendering no reporter enzyme activity under inducing conditions.

In addition to their applications for enzymatic assays in vitro, by using histochemical substrates such as X-Gluc for GUS, the protease detectors of the invention can be used to detect and quantitate cell-specific induction of protease activities in transformed organisms. In addition, through the selection and use of distinct enzymes that can work with fluorogenic or histochemical substrates that can produce products with different colors or chemical properties, the protease detectors of the invention can be used for multiplex analyses of different protease activities in the same cell.

It may also be desirable to design continuous monitoring systems for proteases in eukaryotes. For this purpose, an indirect activation/amplification system may be appropriate. In this approach, a well-defined heterologous transcription factor, such as the yeast transcription factor Gal4 may be fused with the repressor domain via the protease cleavage domain. The transcription factor remains inactive until cleavage from the repressor. As a reporter for the released transcription factor, a reporter gene (e.g., Green Fluorescent Protein or luciferin) expression cassette is placed under the control of a promoter consisting of the DNA responsive element to which the transcription factor binds (e.g., one or more Gal4 operator sequences). It is known that this type of synthetic promoter is stringently dependent on the presence of the transcription factor protein, with little background in either plant or animal cells. These constructs are thereafter introduced into cells of interest, where they are expressed. This strategy enables continuous monitoring of the level of a particular protease activity via detection of the reporter gene product in the cells. If differentiable detectable reporters are used (e.g., different spectral variants of GFP), the large numbers of well-characterized transcription regulators from bacteria and fungi should allow monitoring of the activities of multiple proteases simultaneously. This assay system can be employed using any of the numerous well-characterized transcription factor systems presently available in the art.

Test kits are also provided in accordance with the present invention, to facilitate the use of the protease detector in cell-free or cell-based assays such as those described above. In a preferred embodiment, the kit is a protease detection kit that comprises a chimeric protease detector protein as describe above, along with instructions on how to use the protein to detect the presence or activity of a pre-determined protease and, optionally, further comprises at least one other reagent useful for conducting assays to detect the presence or activity of a protease. In a particularly preferred embodiment, the test kit is adapted for detection of a plurality of pre-determined proteases, and comprises two or more different protease detector proteins.

The invention provides another test kit useful for continuous monitoring of protease activity in a selected cell type. This kit provides a protease detector system having two constructs; one in which a transcription factor is linked to a repressor moiety via the protease cleavage site, and the other comprising a reporter gene under the control of a promoter and the DNA responsive element activated by binding of the transcription factor. This kit also may provide selected cell types for practicing the assay, along with various reagents for culturing the cells, introducing the constructs into the cells, and detecting expression of the reporter gene.

The following example is provided to describe the invention in greater detail. It is intended to illustrate, not to limit, the invention.

EXAMPLE 1

HBD/GUS Construct for Detecting Active Caspase

In this example, it is experimentally determined whether the HBD of GR and other steroid receptors could possibly act as general repressor domains that could be used to mask the enzyme activities of a protein fusion partner. The placement of a defined protease target site sequence between the two partners would then release the latent enzymatic activity from repression by the HBD and the associated HSP90.

A prerequisite for the strategy is the accessibility of the protease target site in the fusion protein and the ability of the released enzyme to regain its active state. Prior to the experimental results reported herein, it was entirely unclear whether the cleavage site would be available or, if available, if the released reporter enzyme would be active. We proceeded to test this approach by the strategy outlined in FIG. 1. Since Caspase-1 from animal systems have been well characterized, we chose its target sequence Tyr-Val-Ala-Asp-Gly (SEQ ID NO:21) as our first test case. The coding sequence for the bacterial enzyme β-glucuronidase (GUS) is fused to the HBD of GR with the peptide sequence Tyr-Val-Ala-Asp-Gly (SEQ ID NO:21) as a linker between the two partners of the chimera. As a negative control for sequence specific cleavage by caspase-1, an almost identical fusion protein between GUS and the HBD is created with the linker Tyr-Val-Ala-Ala-Gly (SEQ ID NO:22). The conversion of the aspartate at the P1 position in the linker is predicted to abolish cleavage by caspase-1. If our strategy is operating as designed, we would predict that the two fusion proteins will both be inactive upon their synthesis in the presence of HSP90. Upon addition of caspase-1, the cleavage of the Tyr-Val-Ala-Asp-Gly (SEQ ID NO:21) sequence may lead to the appearance of GUS activity while the fusion with the Tyr-Val-Ala-Ala-Gly (SEQ ID NO:22) linker should be unaffected.

Figure 2A:
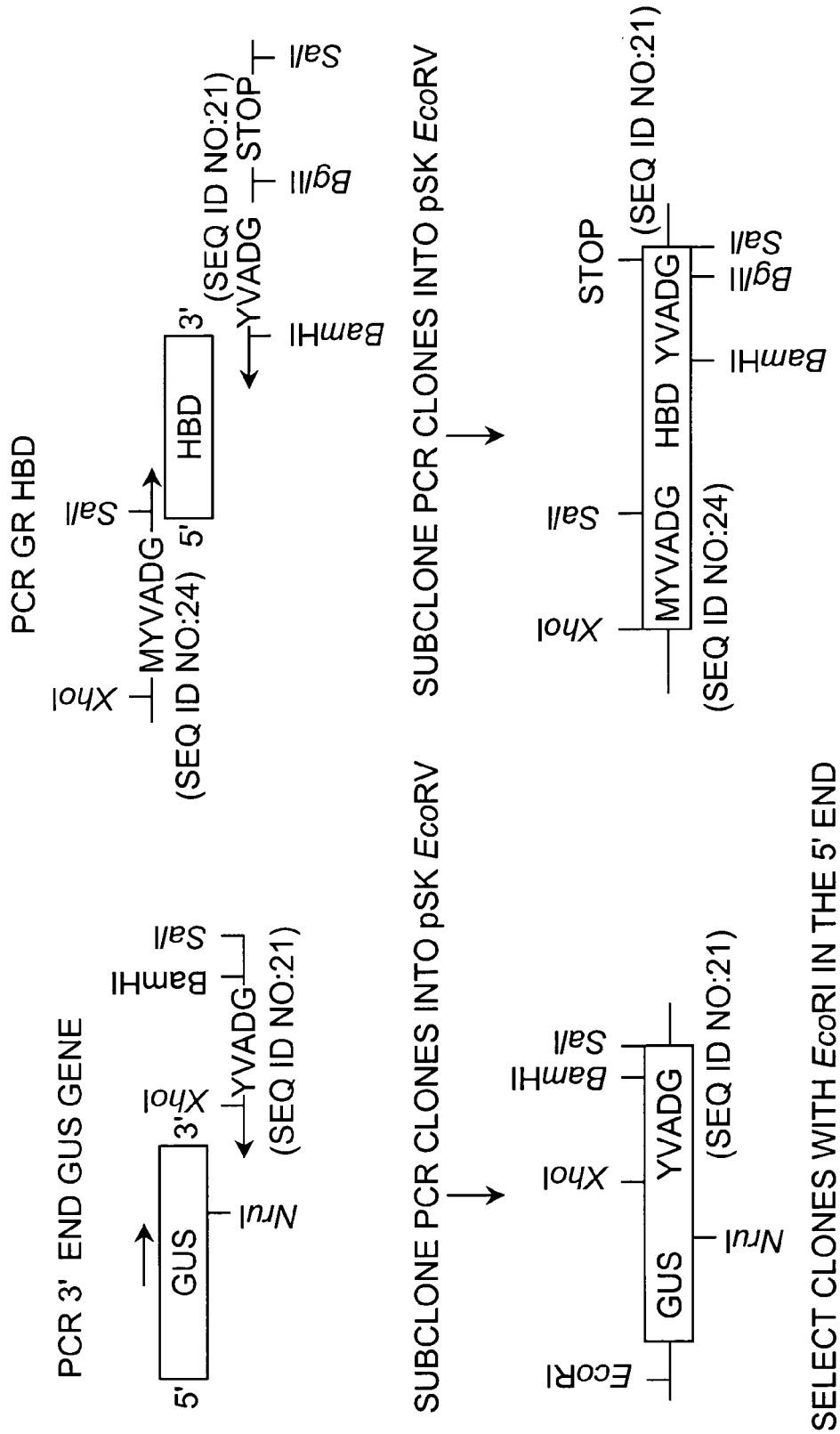
FIG. 2A: shows step 1, introduction of the caspase target cleavage site by polymerase chain reaction (PCR).
Figure 2B:
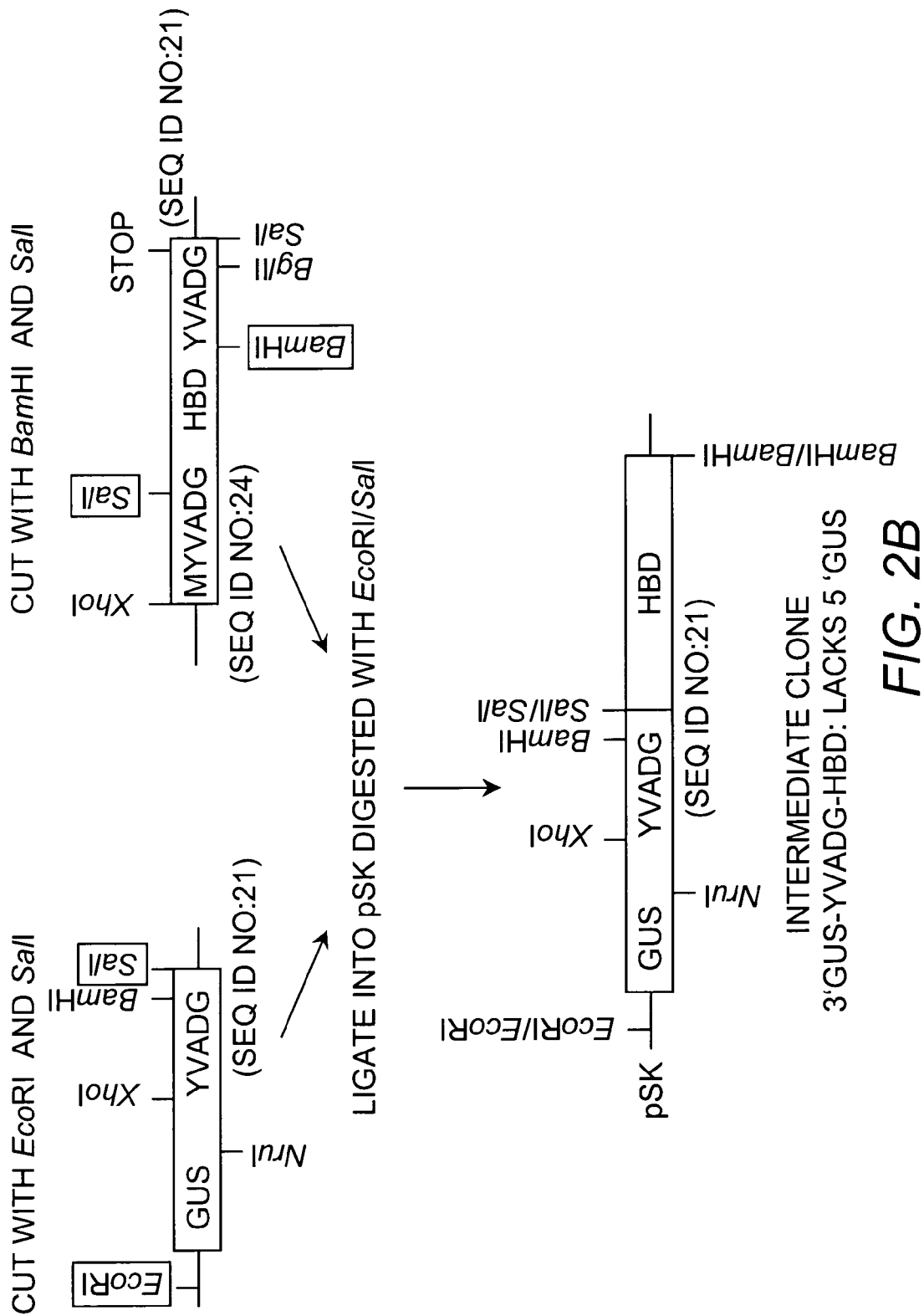
FIG. 2B: shows step 2, creating an intermediate chimeric clone, 3'GUS-YVADG-HBD.
Figure 2C:
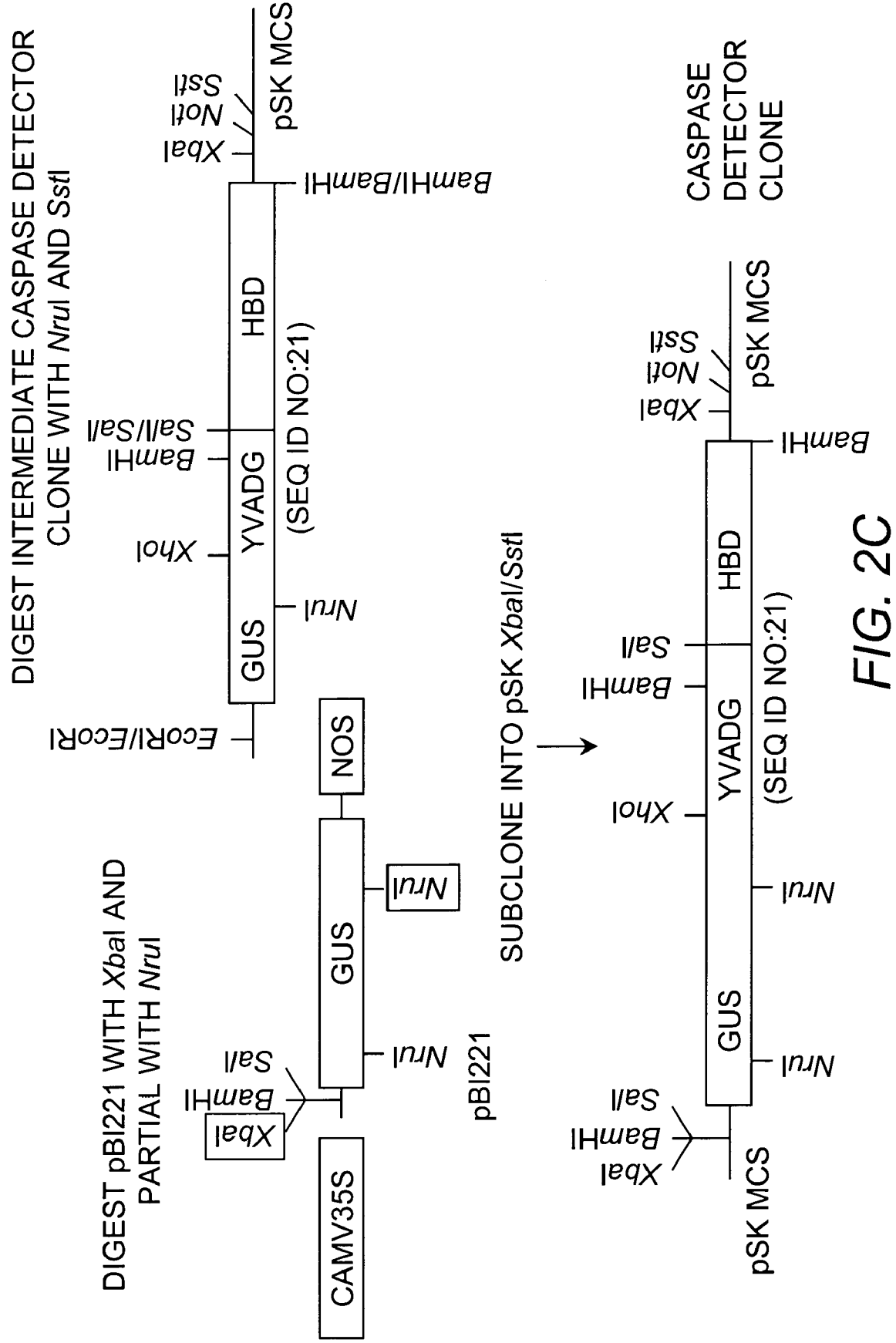
FIG. 2C: shows step 3, 5' end GUS gene reconstruction.

The method for the construction of the fusion proteins are described in FIG. 2. In the first step, the caspase target sequence and its P1 variant are introduced to the 3' end of the GUS gene and the two ends of the GR-HBD coding sequence via PCR amplification using synthetic oligonucleotide primers. These clones allow one to create either N-terminal or C-terminal fusions between the two partners with the same protease target site as linker in both cases. For the present work, we only created and tested fusions with GUS as the N-terminal partner. In step II, the 3' portion of GUS with the appropriate protease site linker is fused with the HBD to generate a partial fusion. The full length GUS coding sequence is then reconstituted in Step III by subcloning into the appropriate sites of the vector pBI221. This strategy avoids the need to amplify the complete coding sequence for GUS each time a new linker sequence needs to be constructed.

Figure 3:
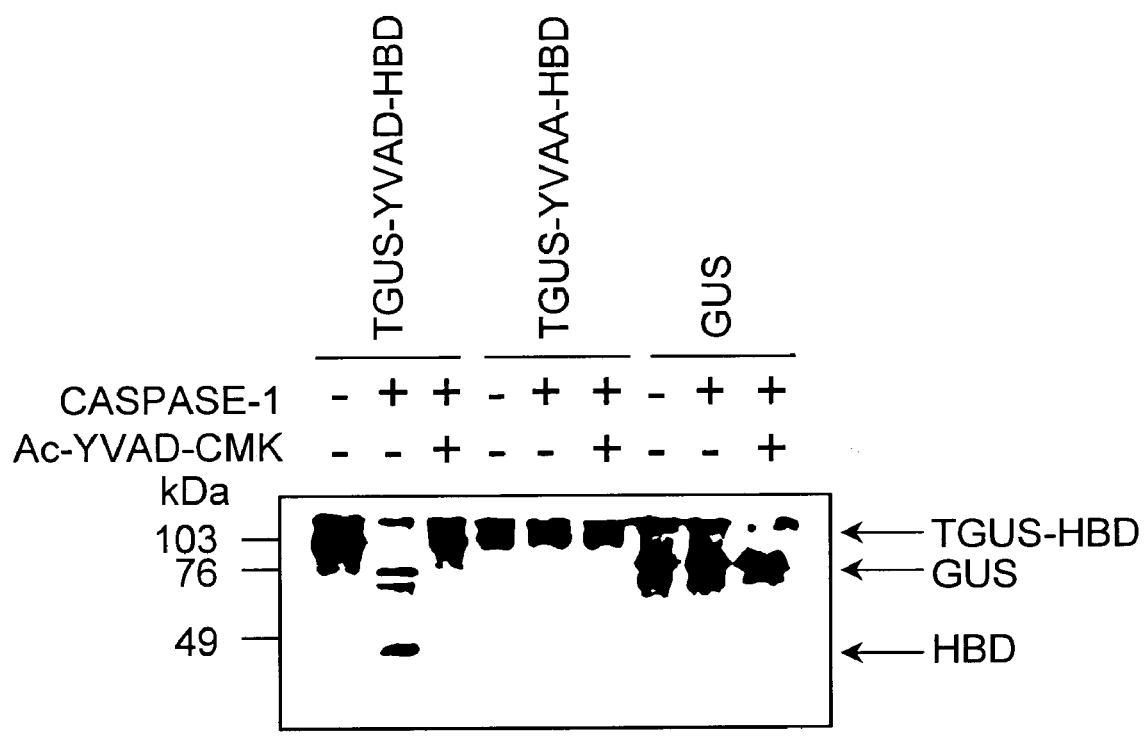
FIG. 3. Autoradiogram of SDS-PAGE gel demonstrating that the linker site between GUS and GR-HBD can be specifically recognized and cleaved by purified caspase-1. Lefthand 3 lanes show protease detector GUS-YVAD-HBD, in the presence or absence of caspase-1 and/or a peptide inhibitor of caspase-1, AcYVAD-CMK; center 3 lanes show control construct GUS-YVAA-HBD that is not recognized by caspase-1, in the presence or absence of caspase-1 and/or a peptide inhibitor of caspase-1; righthand 3 lanes show GUS alone, in the presence or absence of caspase-1 and/or a peptide inhibitor of caspase-1.

FIG. 3 presents the results that demonstrate the linker site between GUS and GR-HBD can be specifically recognized and cleaved by purified caspase-1. The two fusion constructs as well as GUS alone were inserted into a pET vector (Novagen) for T7 RNA polymerase dependent in vitro transcription/translation using a coupled rabbit reticulocyte lysate system (Promega). To visualize the translated proteins, [35S]methionine was incorporated into the newly synthesized products. FIG. 3 shows that fusion proteins of about 100 kDa were produced with the two constructs while the GUS alone construct produced a protein with an apparent mass of about 70 kDa. Addition of purified caspase-1 generated cleavage products of 70 kDa and about 30 kDa from the Tyr-Val-Ala-Asp-Gly (SEQ ID NO:21) containing fusion but not the P1 linker variant. In fact, no obvious proteolysis was detected by caspase-1 was observed with either the P1 linker mutant fusion or the GUS alone control. As expected, the cleavage of the Tyr-Val-Ala-Asp-Gly (SEQ ID NO:21) containing fusion protein by caspase-1 can be inhibited by addition of the caspase specific peptide inhibitor YVAD-emk.

Figure 4A:
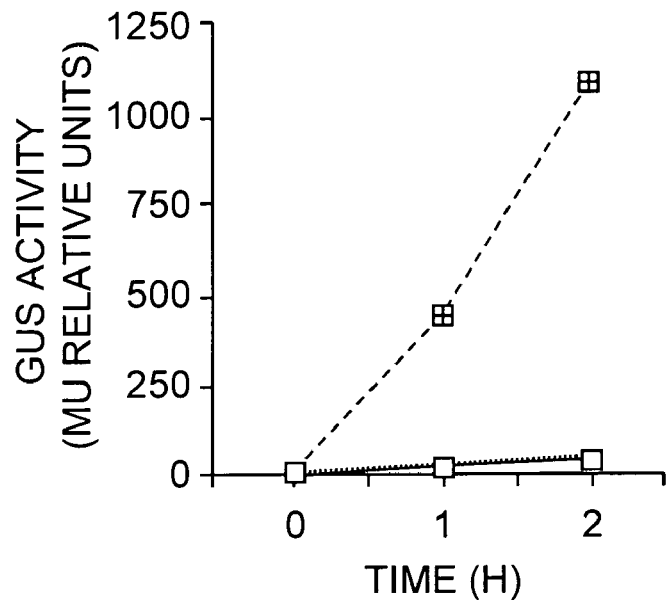
FIG. 4A shows results of an experiment in which reticulocyte lysate alone, or expressing the caspase-1 detector construct in the presence of caspase, were examined for GUS activity.
Figure 4B:
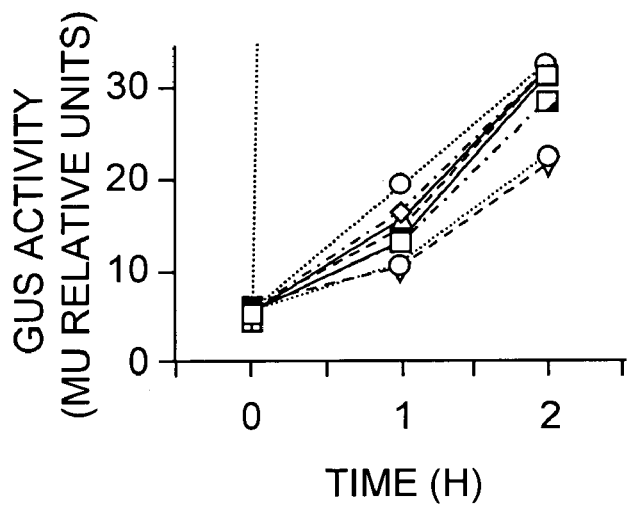
FIG. 4B shows results of a second experiment that tested GUS activity in in vitro translations using a variety of control and test combinations. Legend: Ret=reticulocyte lysate; casp1=caspase-1; Ac-YVAD-CMK=peptide inhibitor of caspase-1; TGUS-YVAD-HBD=the caspase-1 protease detector; C=conrol (no caspase-1); TGUS-YVAA-HBD=the caspase-1 protease detector control construct.

To assay for the activity of the fusion proteins, we carried out in vitro transcription/translation of the different constructs without radiolabelled methionine. The results are presented in FIG. 4. In the absence of caspase-1, either fusion protein show essentially no significant GUS activity above the low background present in reticulocyte lysates alone. In a separate experiment, we found that transcription/translation with the GUS alone control can produce high GUS activity with this assay system (data not shown). Thus, the absence of GUS activity with the fusion proteins is likely due to the inactivation of the GUS partner by its fusion to the GR-HBD domain and not due to the presence of inhibitory compounds in the lysate. Upon addition of caspase-1 to the Tyr-Val-Ala-Asp-Gly (SEQ ID NO:21) containing fusion protein, a dramatic appearance of GUS is observed. This is in contrast to the Tyr-Val-Ala-Ala-Gly (SEQ ID NO:22) containing fusion protein, in which case no detectable increase in GUS activity is observed. The unmasking of the GUS activity in the fusion is due to the proteolytic cleavage by the added caspase-1 since inclusion of the caspase specific inhibitor YVAD-cmk abolishes this process. These results demonstrate that the released GUS enzyme partner can function properly as a reporter of active caspase cleavage.

In this example, we documented the successful application of the steroid hormone receptor as a sensitive reporter system to detect active protease in vitro. Using GUS as a model reporter, we found that fusion of the GR-HBD can effectively mask the intrinsic enzyme activity of the GUS partner in the chimeric protein produced in the rabbit reticulocyte lysate system. Quantitative kinetic analysis of GUS enzyme activity demonstrated no detectable cleavage of the fluorogenic substrate 4-MUG by the fusions. The tightness of this repression by the HBD domain is likely linked to the fact that the GUS protein needs to dimerize in order to form the active enzyme. Our observation thus indicate that there is a likely excess of HSP90 in the lysate that we used to produce the fusion protein in vitro. The effective sequestration of the translated GUS-HBD fusion protein by the presumed association with HSP90 then resulted in complete suppression of GUS enzymatic activity. These in vitro results are corroborated by our analyses with transgenic plants (specifically tobacco and *Arabidopsis*), in which the GUS-HBD fusions were expressed under a strong constitutive viral promoter. Although these plants were found by RNA gel blot analyses to express high levels of transcripts for the transgene, little GUS activity can be detected (data not shown). This result suggests that the GR-HBD domain can also effectively repress the GUS fusion partner when expressed in eukaryotic cells, identical to our observation in vitro.

Previous work with chimeric fusions of steroid receptor HBDs have documented that addition of the appropriate hormone can relieve the repressive function of this domain on the fusion partner. However, it was not clear that the linker region between the two partners in the chimera can in fact be accessible to externally added enzymes such as proteases. Our present work demonstrated that insertion of a protease site into this junction region is in fact quite readily cleaved in a specific manner by added protease. Furthermore, the separated reporter protein readily regained its activity. Addition of an inhibitor specific for the added protease inhibited cleavage of the fusion protein and abolished the activation of the latent enzyme activity. These results thus demonstrated that the HBD of steroid hormones can be linked to various reporter enzymes such as GUS to provide a variety of chimeric protease reporters.

REFERENCES

Aoyama T and Chua N-H (1997) A glucocorticoid-mediated transcriptional induction system in transgenic plants. Plant J. 11: 605-612.

Cryns V and Yuan J (1998) Proteases to die for. Genes and Dev. 12: 1551-1570.

del Pozo O and Lam E (1998) Caspases and programmed cell death in the hypersensitive response of plants to pathogens. Curr. Biol. 8: 1129-1132.

Heim R and Tsien R Y (1996) Engineering green fluorescent protein for improved brightness, longer wavelengths and fluorescence resonance energy transfer. Curr. Biol 6: 178-182.

Mattioni T, Louvion J-F and Picard D (1994) Regulation of protein activities by fusion to steroid binding domains. in Methods in Cell Biology 43: 335-352.

Simon R., Igeno M I and Coupland G (1996) Activation of floral meristem identity gene in Arabidopsis. Nature 384: 59-62.

Talanian R V, Quinlan C, Trautz S, Hackett M C, Mankovich J A, Banach D, Ghayur T, Brady K D and Wong W W (1997) Substrate specificities of caspase (interleukin-1b converting enzyme) family proteases. J. of Biol. Chem. 272: 9677-9682.

The present invention is not limited to the embodiments described and exemplified above, but is capable of variation and modification without departure from the scope of the appended claims.

We claim:

1. A chimeric protein for detecting the presence or activity of a pre-determined protease, which comprises:
   a) a cellular receptor repressor domain which represses activity of a normally biologically active protein fused thereto, wherein the repressor domain is obtained from a steroid hormone receptor or a bHLH/PAS transcription regulator;
   b) a reporter domain comprising a protein having a detectable biological activity when not fused to the repressor domain, wherein said reporter domain comprises β-glucuronidase; and
   c) a protease cleavage domain linking the repressor domain to the reporter domain, the protease cleavage domain comprising a structure that is cleaved by activity of the pre-determined protease.

2. The chimeric protein of claim 1, wherein the protease cleavage domain comprises a cleavage site for a caspase.

3. The chimeric protein of claim 1, which further comprises a spacer between the protease cleavage domain and one or both of the repressor domain and the reporter domain.

4. The chimeric protein of claim 1, which comprises at least one repressor domain and a plurality of reporter domains, each linked to the at least one repressor domain by a protease cleavage site.

5. The chimeric protein of claim 4, wherein the plurality of reporter domains are different from one another.

6. The chimeric protein of claim 4, wherein the protease cleavage sites are different from one another.

7. A chimeric protein for measuring caspase activity, comprising a hormone binding domain linked to a β-glucuronidase enzyme by a peptide comprising a caspase cleavage site, wherein the β-glucuronidase is inactive due to linkage to the hormone binding domain and release of the β-glucuronidase through caspase cleavage of the cleavage site restores activity of the β-glucuronidase.

* * * * *

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: synthetic sequence; caspase-1 cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 1

Tyr Val Ala Asp Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic sequence; caspase-2 cleavage domain
<220> FEATURE:
<221> NAME/KEY: MISC_FEATURE
<222> LOCATION: (6)..(6)
<223> OTHER INFORMATION: "Xaa" represents any amino acid

<400> SEQUENCE: 2

Val Asp Val Ala Asp Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic sequence; caspase-3 cleavage domain
<220> FEATURE:
<221> NAME/KEY: MISC_FEATURE
<222> LOCATION: (5)..(5)
```

```
<223> OTHER INFORMATION: "Xaa" represents any amino acid

<400> SEQUENCE: 3

Asp Glu Val Asp Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic sequence; caspase-4 cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 4

Leu Glu Val Asp Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic sequence; caspase-5 cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 5

Trp Glu His Asp Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic sequence; caspase-6 cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 6

Val Glu Ile Asp Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic sequence; caspase-7  cleavage domain
<220> FEATURE:
<221> NAME/KEY: MISC_FEATURE
<222> LOCATION: (6)..(6)
<223> OTHER INFORMATION: "Xaa" represents any amino acid

<400> SEQUENCE: 7

Val Asp Gln Val Asp Xaa
1               5

<210> SEQ ID NO 8
<211> LENGTH: 5
<212> TYPE: PRT
```

```
<213> ORGANISM: Artificial Sequence
<220> FEATURE:
<223> OTHER INFORMATION: synthetic sequence; caspase-8 cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 8

Ile Glu Thr Asp Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic sequence; caspase-9 cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 9

Leu Glu His Asp Xaa
1               5

<210> SEQ ID NO 10
<211> LENGTH: 4
<212> TYPE: PRT
<213> ORGANISM: Artificial Sequence
<220> FEATURE:
<223> OTHER INFORMATION: synthetic sequence; calpain cleavage domain
<220> FEATURE:
<221> NAME/KEY: MISC_FEATURE
<222> LOCATION: (4)..(4)
<223> OTHER INFORMATION: "Xaa" represents any amino acid

<400> SEQUENCE: 10

Val Leu Lys Xaa
1

<210> SEQ ID NO 11
<211> LENGTH: 5
<212> TYPE: PRT
<213> ORGANISM: Artificial Sequence
<220> FEATURE:
<223> OTHER INFORMATION: synthetic sequence; cathepsin-G cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 11

Ala Val Pro Phe Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic sequence; collagenase cleavage domain
<220> FEATURE:
<221> NAME/KEY: MISC_FEATURE
<222> LOCATION: (8)..(8)
<223> OTHER INFORMATION: "Xaa" represents any amino acid

<400> SEQUENCE: 12

Pro Gln Gly Ile Ala Gly Gln Xaa
```

```
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic sequence; elastase I cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 13

Ala Ala Pro Val Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic sequence; elastase II cleavage domain
<220> FEATURE:
<221> NAME/KEY: MISC_FEATURE
<222> LOCATION: (5)..(5)
<223> OTHER INFORMATION: "Xaa" represents any amino acid

<400> SEQUENCE: 14

Ala Ala Pro Ala Xaa
1               5

<210> SEQ ID NO 15
<211> LENGTH: 4
<212> TYPE: PRT
<213> ORGANISM: Artificial Sequence
<220> FEATURE:
<223> OTHER INFORMATION: synthetic sequence; granzyme B cleavage domain
<220> FEATURE:
<221> NAME/KEY: MISC_FEATURE
<222> LOCATION: (4)..(4)
<223> OTHER INFORMATION: "Xaa" represents any amino acid

<400> SEQUENCE: 15

Ala Ala Asp Xaa
1

<210> SEQ ID NO 16
<211> LENGTH: 9
<212> TYPE: PRT
<213> ORGANISM: Artificial Sequence
<220> FEATURE:
<223> OTHER INFORMATION: synthetic sequence; MMP-1 cleavage domain
<220> FEATURE:
<221> NAME/KEY: VARIANT
<222> LOCATION: (8)..(8)
<223> OTHER INFORMATION: d Arginine
<220> FEATURE:
<221> NAME/KEY: MISC_FEATURE
<222> LOCATION: (9)..(9)
<223> OTHER INFORMATION: "Xaa" represents any amino acid

<400> SEQUENCE: 16

Pro Gln Gly Ile Ala Gly Gln Arg Xaa
1               5

<210> SEQ ID NO 17
<211> LENGTH: 4
<212> TYPE: PRT
<213> ORGANISM: Artificial Sequence
```

```
<220> FEATURE:
<223> OTHER INFORMATION: synthetic sequence; kallicrein cleavage domain
<220> FEATURE:
<221> NAME/KEY: MISC_FEATURE
<222> LOCATION: (4)..(4)
<223> OTHER INFORMATION: "Xaa" represents any amino acid

<400> SEQUENCE: 17

Pro Phe Arg Xaa
1

<210> SEQ ID NO 18
<211> LENGTH: 7
<212> TYPE: PRT
<213> ORGANISM: Artificial Sequence
<220> FEATURE:
<223> OTHER INFORMATION: synthetic sequence; papain cleavage domain
<220> FEATURE:
<221> NAME/KEY: MISC_FEATURE
<222> LOCATION: (7)..(7)
<223> OTHER INFORMATION: "Xaa" represents any amino acid

<400> SEQUENCE: 18

Gln Val Val Ala Gly Ala Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic sequence; renin cleavage domain
<220> FEATURE:
<221> NAME/KEY: MISC_FEATURE
<222> LOCATION: (9)..(9)
<223> OTHER INFORMATION: "Xaa" represents any amino acid

<400> SEQUENCE: 19

Arg Pro Phe His Leu Leu Val Tyr Xaa
1               5

<210> SEQ ID NO 20
<211> LENGTH: 4
<212> TYPE: PRT
<213> ORGANISM: Artificial Sequence
<220> FEATURE:
<223> OTHER INFORMATION: synthetic sequence; thrombin cleavage domain
<220> FEATURE:
<221> NAME/KEY: MISC_FEATURE
<222> LOCATION: (4)..(4)
<223> OTHER INFORMATION: "Xaa" represents any amino acid

<400> SEQUENCE: 20

Val Pro Arg Xaa
1

<210> SEQ ID NO 21
<211> LENGTH: 5
<212> TYPE: PRT
<213> ORGANISM: Artificial Sequence
<220> FEATURE:
<223> OTHER INFORMATION: synthetic sequence; caspase-1 cleavage domain

<400> SEQUENCE: 21

Tyr Val Ala Asp Gly
1               5

<210> SEQ ID NO 22
<211> LENGTH: 5
```

```
<212> TYPE: PRT
<213> ORGANISM: Artificial Sequence
<220> FEATURE:
<223> OTHER INFORMATION: synthetic sequence; caspase-1 cleavage domain
      variant

<400> SEQUENCE: 22

Tyr Val Ala Ala Gly
1               5

<210> SEQ ID NO 23
<211> LENGTH: 4
<212> TYPE: PRT
<213> ORGANISM: Artificial Sequence
<220> FEATURE:
<223> OTHER INFORMATION: synthetic sequence; caspase-1 cleavage product

<400> SEQUENCE: 23

Tyr Val Ala Asp
1

<210> SEQ ID NO 24
<211> LENGTH: 6
<212> TYPE: PRT
<213> ORGANISM: Artificial Sequence
<220> FEATURE:
<223> OTHER INFORMATION: synthetic sequence; caspase-1 cleavage domain

<400> SEQUENCE: 24

Met Tyr Val Ala Asp Gly
1               5
```